(12) United States Patent
Wong (10) Patent No.: US 8,408,427 B2
(45) Date of Patent: Apr. 2, 2013

(54) SINGLE DOSE NASAL SPRAY PUMP

(75) Inventor: Paxton Wong, Maroubra (AU)

(73) Assignee: MK International Pty Ltd, Maroubra, NSW (AU)

( * ) Notice: Subject to any disclaimer, the term of this patent is extended or adjusted under 35 U.S.C. 154(b) by 573 days.

(21) Appl. No.: 12/576,835

(22) Filed: Oct. 9, 2009

(65) Prior Publication Data

US 2011/0057055 A1 Mar. 10, 2011

(30) Foreign Application Priority Data

Sep. 7, 2009 (AU) ................................ 2009904247

(51) Int. Cl.
*B05B 9/00* (2006.01)
(52) U.S. Cl. ...................... 222/321.6; 222/320; 239/329
(58) Field of Classification Search ............... 222/321.6, 222/386, 325–327, 320, 321.1, 321.2, 321.7–321.9, 222/372, 382, 383.1, 383.3; 239/329
See application file for complete search history.

(56) References Cited

U.S. PATENT DOCUMENTS

| | | | | |
|---|---|---|---|---|
| 4,532,967 A * | 8/1985 | Graf | .................................. | 141/3 |
| 4,694,977 A * | 9/1987 | Graf et al. | ..................... | 222/259 |
| 4,762,475 A * | 8/1988 | Fuchs | ........................... | 417/550 |
| 4,830,284 A * | 5/1989 | Maerte | ......................... | 239/333 |
| 4,896,799 A * | 1/1990 | Giuffredi | .................. | 222/321.2 |
| 6,257,454 B1 * | 7/2001 | Ritsche | ................... | 222/153.13 |
| 6,851,583 B2 * | 2/2005 | Masuzzo et al. | ........... | 222/321.6 |
| 7,299,949 B2 * | 11/2007 | Greiner-Perth | .......... | 222/153.13 |
| 7,520,409 B2 * | 4/2009 | Bougamont et al. | ....... | 222/321.9 |
| 8,136,703 B2 * | 3/2012 | Kamishita | ..................... | 222/256 |

FOREIGN PATENT DOCUMENTS

WO WO2007123207 * 11/2007

* cited by examiner

*Primary Examiner* — Kevin P Shaver
*Assistant Examiner* — Donnell Long
(74) *Attorney, Agent, or Firm* — Pillsbury Winthrop Shaw Pittman LLP (57) ABSTRACT

In one or more embodiments a single dose nasal spray pump includes a reservoir configured for holding a single dose of material to be dispensed, the reservoir extending between a closed end and an open end; a cap to be configured to be disposed over the open end of the reservoir, the cap including an aperture; a stem extending between an outlet end and a lower end, the stem having a conduit extending from the outlet end of the stem to a conduit inlet at or adjacent the lower end of the stem; and a piston disposed about the stem and configured for movement between a first position wherein the piston seals or substantially seals the conduit inlet and a second position wherein the piston is remote from the conduit inlet; wherein the stem is configured for movement from a first stem position wherein the piston is disposed in the reservoir in the first piston position and a second stem position wherein the stem is moved toward the closed end of the reservoir such that the piston is moved into the second piston position.

20 Claims, 7 Drawing Sheets

SINGLE DOSE NASAL SPRAY PUMP

FIELD OF THE INVENTION

The present invention relates to intranasal substance delivery systems and, in particular, to a nasal spray pump system.

The invention has been developed primarily to allow nasal delivery of a single dose of therapeutic substance and will be described hereinafter with reference to this application. However, it will be appreciated that the invention is not limited to this particular field of use and is capable of the nasal delivery of non-therapeutic substances.

BACKGROUND OF THE INVENTION

Of recent times, it has become apparent that many pharmaceutical substances such as insulin, hormones, asthma treatments, lipophyllic drugs, opiates, erectile dysfunction medication, migraine medication or other therapeutic substances can be efficaciously delivered intranasally. This offers significant advantage, for example, where diabetics can intranasally receive insulin rather than subcutaneously by means of a needle.

This particular advantage is also provided for the use of hormone treatments amongst many other therapeutic substances. It is desired that a regular user can simply have provided an intranasal delivery device so that at any convenient time a dose of therapeutic substance can be taken. It will be appreciated that significantly less privacy is required to intranasally deliver a therapeutic substance as opposed to that required to inject the same substance via a syringe, and that hygiene requirements are reduced.

It is undesirable to expose a therapeutic substance user to the possibility of intranasally consuming more of the substance than is desired. BD Medical Pharmaceutical Systems of France offer for sale under the trademark ACCUSPRAY a nasal spray system which allows the delivery of therapeutic materials. The BD Medical Pharmaceutical Systems nasal spray pump is a syringe type device configured to receive a cartridge containing a single dose of a therapeutic substance. The intranasal spray device receives the cartridge longitudinally and the cartridge is configured to rupture adjacent an opening. The cartridge includes a plunger which is actuated by a secondary plunger on the nasal spray device so as to dispense the therapeutic goods by a plunging action and forcing the contents from the cartridge.

That is, a plunger is longitudinally moved to engage with a cartridge plunger which is linearly moved away from the direction the nasal spray is to be dispensed and is similar to a syringe in function, especially dental syringes configured to receive cartridges of oral anaesthetic. In a dental syringe, the contents of the cartridge are plunged from one end longitudinally and out the other. The BD Medical Pharmaceutical Systems device plunges from one end longitudinally and the contents are forced out the same end through an aperture in the plunger.

A significant disadvantage with this development resides in the single use of the cartridges whereby once the plunger has been plunged it cannot be removed to be re-plunged to allow any unused or undispensed therapeutic goods to be dispensed.

In another attempt at providing a single dose nasal spray system, U.S. Pat. No. 6,948,492 (Wermeling et al) discloses the use of an apparatus for the self-administration of liquid pharmaceutical compositions intranasally. In this patent, a body is configured to contain a plurality of radially extending and circumferentially spaced apart vials each containing a single dose of a therapeutic substance. Each of the vials is sealed in a housing which is electronically controlled to allow rotation of a body cover at predetermined intervals to expose the opening of one of the vials. Each vial includes a plunger having a fluid channel disposed substantially longitudinally through the centre thereof. The channel is configured to receive a needle tip extending from a lower end of a nasal applicator head.

In use, once a vial has been exposed at a predetermined time, the nasal spray applicator head is engaged with the housing so that the needle is received within the fluid channel of the plunger. Movement of the applicator head downwardly toward the bottom of the vial causes the contents of the vial to be plunged through the needle running through the fluid channel and out an aligned channel in the nasal applicator which is configured to be disposed in or adjacent a user's nose.

The lower end of the plunger in each vial includes a recess to receive the nasal spray applicator needle so that once the plunger is fully moved to the bottom of the vial, the needle does not engage with the bottom of the vial so as not to damage the needle or the bottom of the vial.

Unfortunately, the electronic control of this device means that a user needs to wait a predetermined time before being able to access another vial containing therapeutic materials. In the case of a diabetic, for example, this may be particularly undesirable as usage of insulin is not necessarily a function of elapsed time between a previous dose. Furthermore, the use of the needle on the lower end of the nasal applicator is disadvantageous so far as the needle tip is exposed to contamination when removing it from one vial and engaging it with another vial. Yet further, the plunger needs to be made to relatively high tolerances to avoid the needle extending deeper than the plunger when fully plunged.

It will be appreciated that the recess provided to receive the needle tip at the bottom end of the plunger disadvantageously retains some contents of the vial due to its intrinsic nature. Unfortunately, it is not possible to re-actuate the nasal sprayer of either this US patent or the BD Medical Pharmaceutical Systems device by replunging the vial so that any contents that remain cannot be dispensed.

Both the BD Medical Pharmaceutical Systems nasal device and the Wermeling et al device require specialised manufacturing techniques and components to effect these single dose nasal sprayers. Furthermore, it will be appreciated that different sized doses of therapeutic substances cannot be accommodated in either of the prior art nasal sprayers. For example, the Wermeling et al disclosure is limited by the configuration and size available to receive a vial within the housing and the BD Medical Pharmaceutical Systems device can also only take a particular sized dose. It is therefore the case that in order to dispense a plurality of different sized doses, different sized intranasal dispensing apparatus would be required accordingly. This is disadvantageous insofar as it unnecessarily adds to costs in providing different devices for different sized doses.

GENESIS OF THE INVENTION

The genesis of the present invention is a desire to provide a single dose nasal spray device which will overcome or substantially ameliorate one or more of the disadvantages of the prior art, or provide a useful alternative.

SUMMARY OF THE INVENTION

In accordance with a first aspect of the present invention there is provided a single dose nasal spray pump comprising:

a reservoir configured for holding a single dose of material to be dispensed, the reservoir extending between a closed end and an open end;

a cap to be configured to be disposed over the open end of the reservoir, the cap including an aperture;

a stem extending between an outlet end and a lower end, the stem having a conduit extending from the outlet end of the stem to a conduit inlet at or adjacent the lower end of the stem; and a piston disposed about the stem and configured for movement between a first position wherein the piston seals or substantially seals the conduit inlet and a second position wherein the piston is remote from the conduit inlet;

wherein the stem is configured for movement from a first stem position wherein the piston is disposed in the reservoir in the first piston position and a second stem position wherein the stem is moved toward the closed end of the reservoir such that the piston is moved into the second piston position.

In accordance with another aspect of the invention there is provided a nasal spray pump configured to receive a reservoir extending between an open end and a closed end and configured to contain a predetermined dose of material to be delivered intranasally wherein the reservoir is configured to receive a sealing cap over the open end of the reservoir such that the cap includes an aperture, the nasal spray pump comprising:

a stem extending between an outlet end and a lower end, the stem having a conduit extending from the outlet end of the stem to a conduit inlet at or adjacent the lower end of the stem; and a piston disposed about the stem and configured for movement between a first position wherein the piston seals or substantially seals the conduit inlet and a second position wherein the piston is remote from the conduit inlet;

wherein the stem is configured for movement from a first stem position wherein the piston is disposed in the reservoir in the first piston position and a second stem position wherein the stem is moved toward the closed end of the reservoir such that the piston is moved into the second piston position.

It can be seen that there is advantageously provided a single dose nasal spray pump that does not employ piecing needle tips or the like. Furthermore, it will be appreciated that the nasal spray pump advantageously allows the stem to be moved toward the second stem position before providing egress to the material in the reservoir via the stem conduit. Further, it will be appreciated that any preferred sized reservoir containing a predetermined sized dose of material can be used without requiring a new nasal spray pump pumping mechanism.

BRIEF DESCRIPTION OF THE DRAWINGS

Preferred embodiments of the invention will now be described, by way of example only, with reference to the accompanying drawings in which.

DETAILED DESCRIPTION

It will be appreciated that like reference numerals have been used throughout the description of the preferred embodiment to denote like components unless expressly noted otherwise.

Referring to FIGS. 1 to 5, there is shown a nasal spray pump 1 according to the first preferred embodiment. The nasal spray pump 1 includes a reservoir 2 configured for holding a single dose of material (not illustrated) to be dispensed. The reservoir 2 extends between a closed end 3 and an open end 4. A cap 5 is configured to be disposed over the open end 4 of the reservoir 2. The cap 5 includes an aperture 6 centrally disposed on an upper surface 7 of the cap 5.

A stem 9 longitudinally extends between an outlet end 10 and a lower end 11. The stem 9 includes a conduit 12 extending from outlet end 10 of the stem 2 to, or adjacent to, the lower end 11 of the stem. A piston 13 is disposed about the stem 9. The piston 13 is configured to move between a first piston position (as shown in the drawings) wherein the piston 13 seals or substantially seals the conduit 12 inlet at the lower end 11 of the stem 9, and a second piston position (not illustrated) wherein the piston is remote from the conduit 12 inlet at the lower end.

The stem 9 is configured to be retained in the aperture 6 of the cap 5 when the cap 5 is disposed over the open end 4 of the reservoir 2. The stem 9 is also configured for movement through the aperture 6 of the cap 5 between a first stem position (as shown in the drawings) wherein the piston is disposed in the reservoir 2 in the first piston position and a second stem position (not illustrated) wherein the stem 9 is moved toward the closed end 3 of the reservoir 2 where the piston 13 is moved to the second piston position (not illustrated).

Figure 1:
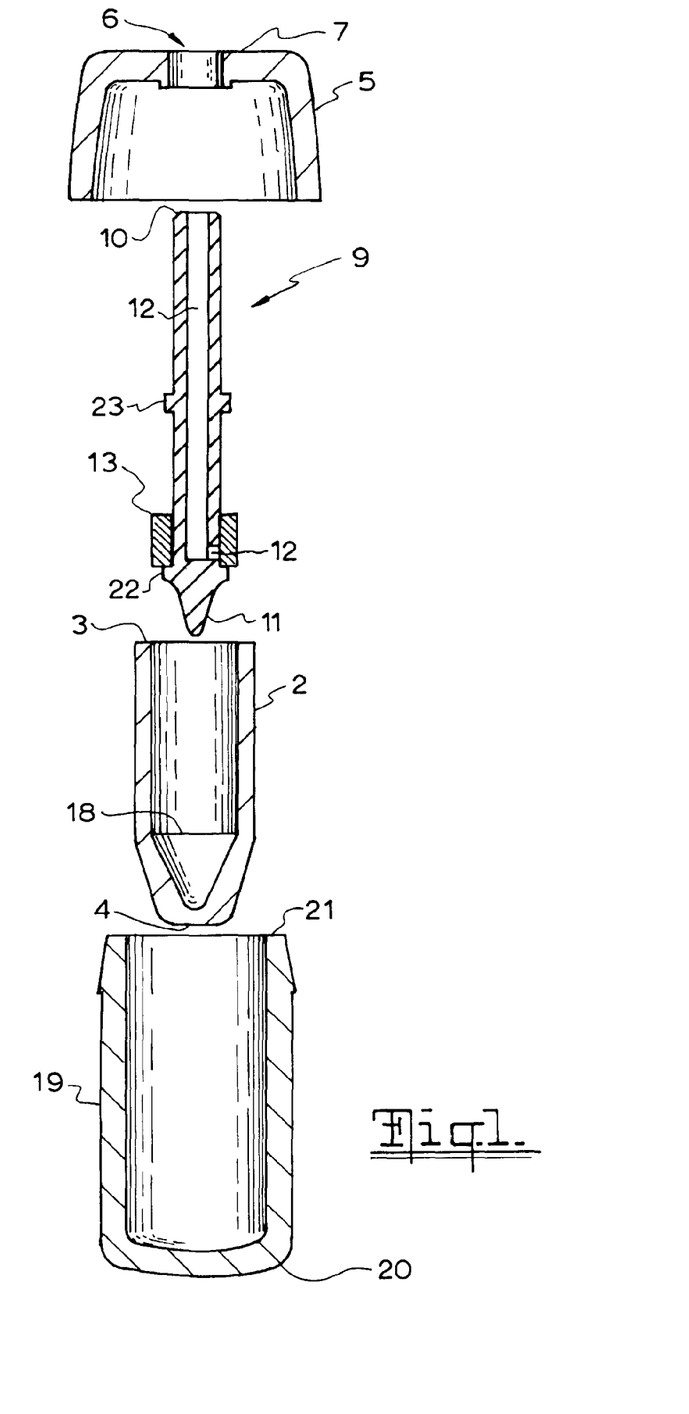
FIG. 1 is a exploded front view of a nasal spray pump according to a first preferred embodiment.
Figure 2:
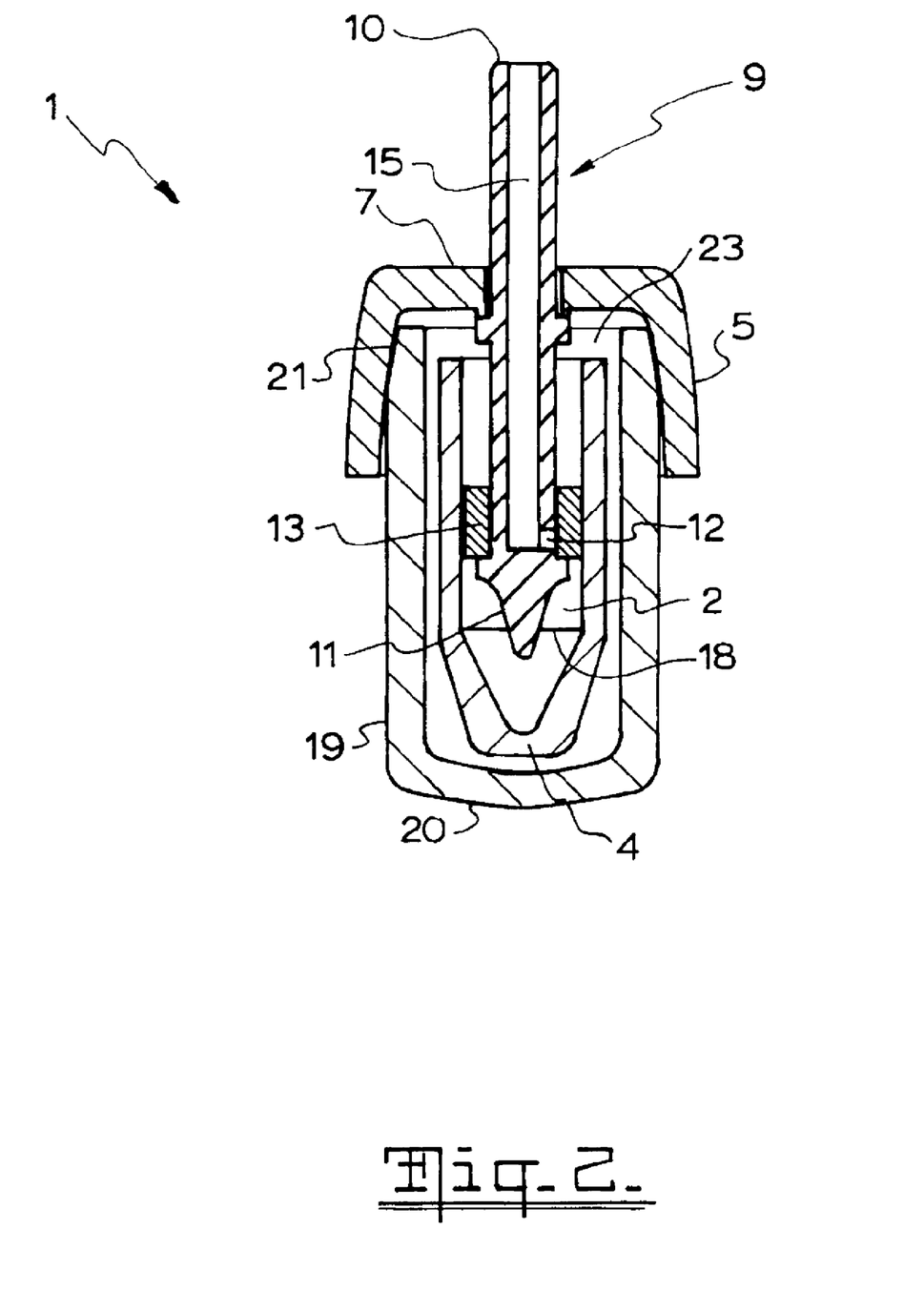
FIG. 2 is a cutaway front view of the nasal spray pump of FIG. 1.
Figure 3:
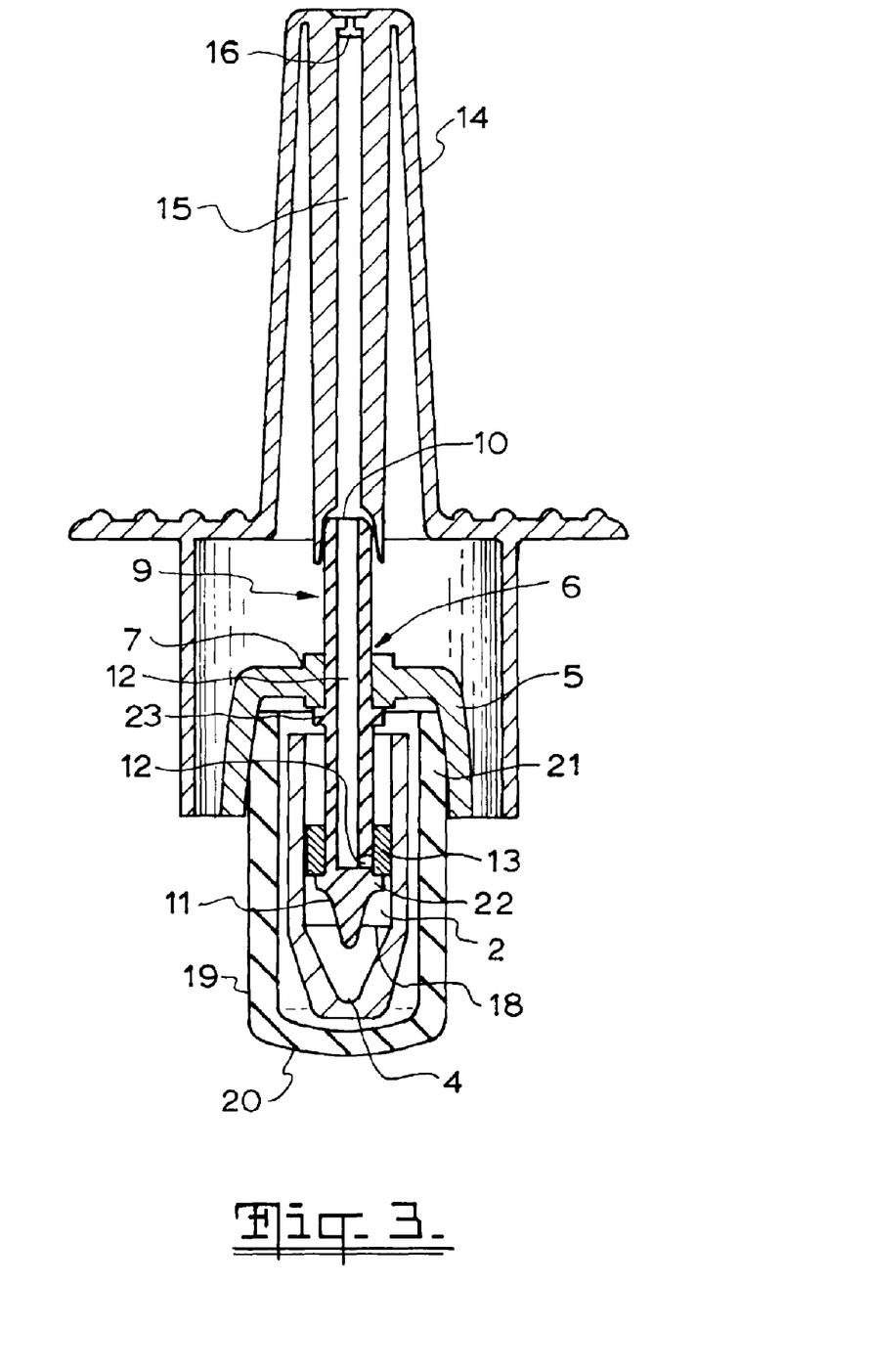
FIG. 3 is a cutaway front view of the nasal spray pump of FIG. 1 with a nasal spray pump head.
Figure 4:
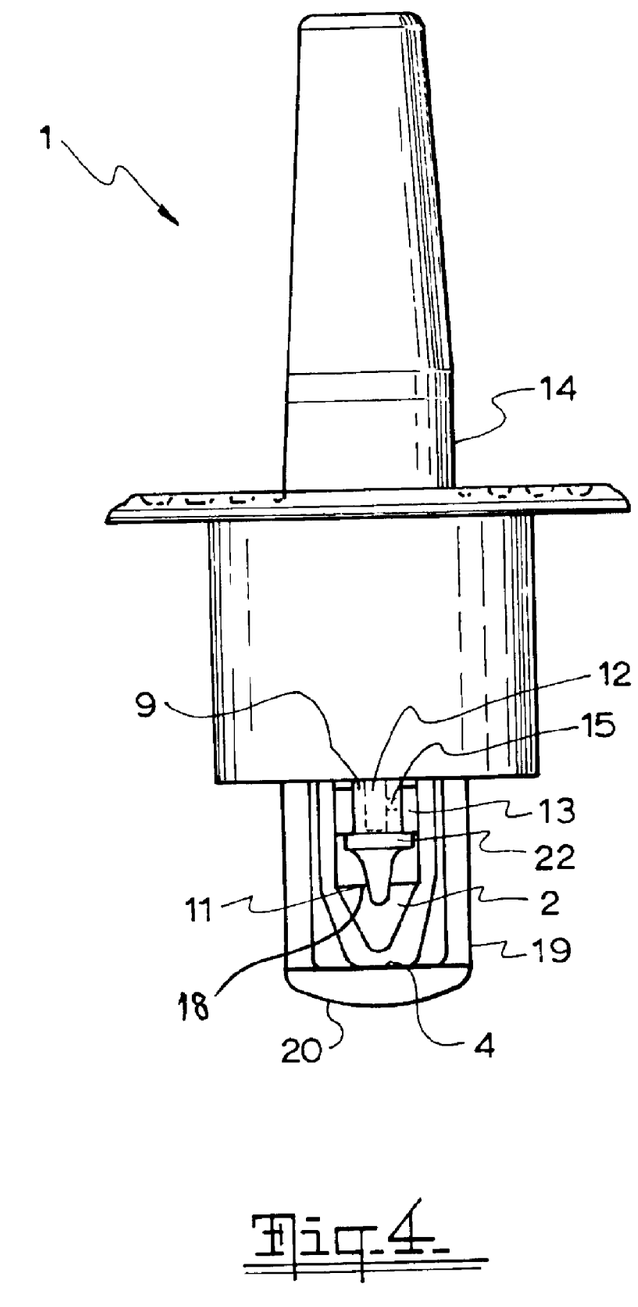
FIG. 4 is a front view of the nasal spray pump of FIG. 3.
Figure 5:
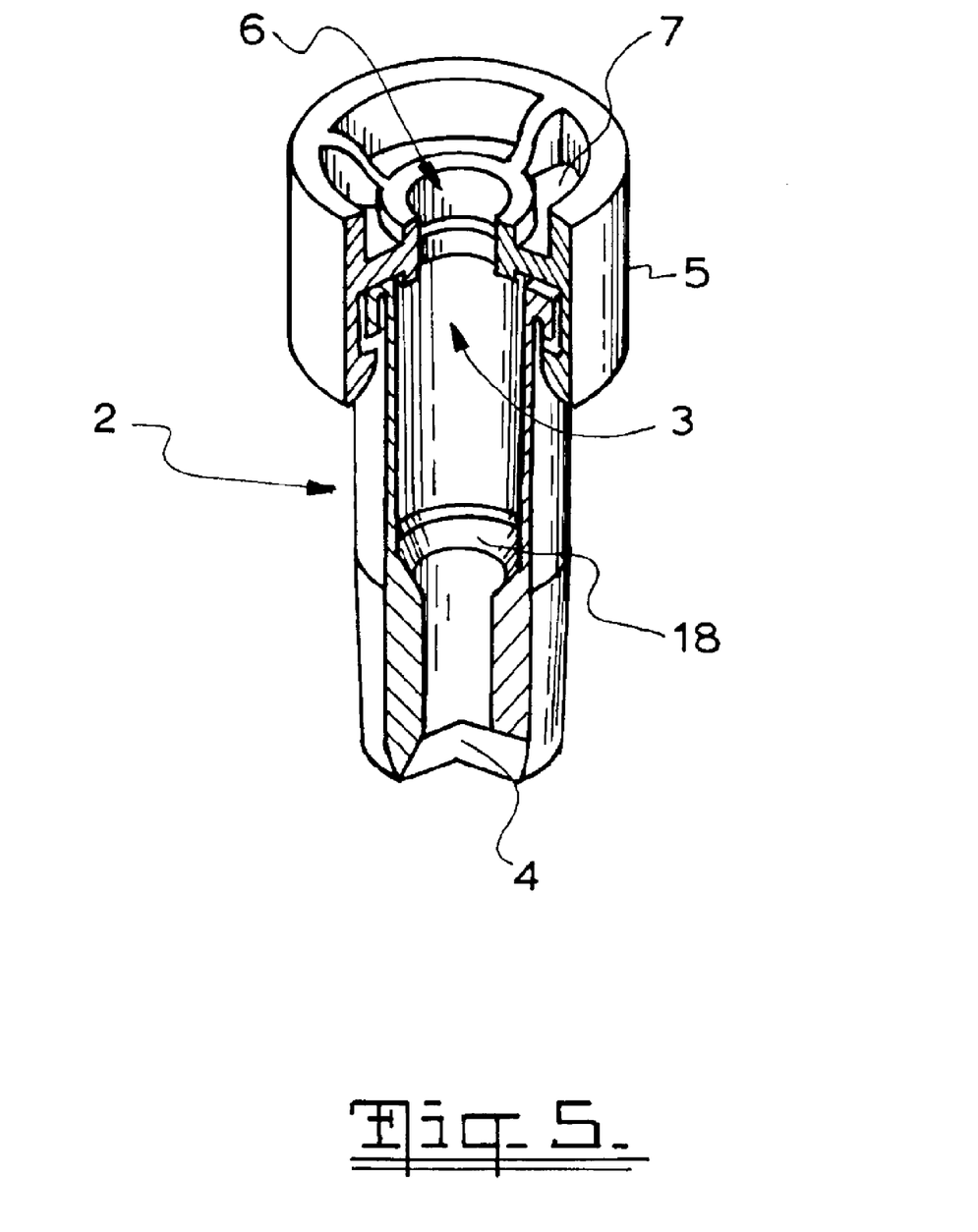
FIG. 5 is an elevated perspective view and partial cutaway of a reservoir and collar according to the preferred embodiment of the nasal spray pump of FIG. 1.

As best shown in FIGS. 3 and 4, the nasal spray pump 1 includes a nasal spray pump head 14 configured to be received by the outlet end 10 of the stem 9. The nasal spray pump head 14 includes a path 15 through which material travelling through the outlet end 10 of the stem 9 can pass and exit at a nasal spray pump head aperture 16 configured to be disposed in or adjacent to a nasal cavity of a user to receive material dispensed therefrom.

A piston engagement means 18 is disposed within the reservoir 2 a predetermined height above the closed end 3. In the preferred embodiment, the piston engagement means 18 is an inwardly circumferentially disposed seat extending radially inwardly a predetermined distance. The piston engagement means 18 extends the predetermined distance such that movement of the stem towards the second stem position causes the piston 13 to engage with the piston engagement means 18 to retain or retard movement of the piston 13 toward the closed end 3 of the reservoir 2. That is, as the stem 9 is moved into the stem second position, the piston 13 engages with the piston engagement means 18 and the stem 9 is continued toward the stem second position with the piston 13 retained thereby exposing the conduit 12 inlet. The conduit 12 is then in communication with the material in the reservoir 2.

As the stem is moved into the stem second position and the piston 13 engages the piston engagement means 18, movement of the stem 9 into the second stem position causes the material disposed in the reservoir 2 to be forced out through the conduit 12 to exit the outlet end 10 of the stem 9. The material then travels through path 15 in the nasal spray pump head 14 to exit at the nasal spray pump head aperture 16 for delivery to a nasal cavity of a user.

The nasal spray pump 1 of the preferred embodiment further includes a canister 19 extending between a closed end 20 and an open end 21. The cap 5 is configured to be disposed over and seal the open end 21 of the canister 19. The cap 5 can be crimped about, or clipped or screwed on to the reservoir 2 and the canister 19 as desired. It will be appreciated that if the reservoir 2 is disposed in the canister 19 that the open end 4 of the reservoir 2 does not need to form a seal with the cap 5 as this function is performed by the upper end 20 of the canister 19. In other embodiments, not illustrated, the cap 5 releasably engages with the canister 19 and/or the reservoir 2 so as to allow for the reservoir 2 to be replaced with a new reservoir having material therein.

The piston 13 is also engaged about the stem 9 in an interference fit so as to provide resistance to movement of the piston 13 from the first piston position where the conduit 12 is sealed by the piston 13.

A lower shoulder 22 is disposed about the stem 9 to provide a seat or stop means to prevent the piston moving down the stem 9 toward the lower end 11. An upper shoulder 23 is disposed about the stem 9 and spaced apart from the lower shoulder 22 toward the outlet end 10 of the stem 9 to prevent movement of the stem 9 away from the closed end 3 of the reservoir 2. This essentially limits the length of travel of the stem 9 within the cap 5 between the first stem position and the second stem position.

The lower end 11 of the stem 9 is shaped to conform to a corresponding shape of the closed end 3 of the reservoir 2. This advantageously provides for the lower end 11 to substantially fill the lower end of the reservoir 2 when the stem 9 is moved to the second stem position. Although the lower end 11 of the stem 9 is shown in the form of a protrusion, this can be substantially flat or any other preferred shape.

It will be appreciated that the piston 13 is not resiliently biased away from the lower end 11 of the stem 9 and that the lower end 11 once the stem 9 has moved into the second stem position is retained in that position. A return spring or other resilient biasing means can be provided to return the stem 9 from the second stem position to the first stem position which is most advantageous in cases where the reservoir 2 is to be interchanged after its contents are dispensed.

However, it will be appreciated that in the case of a single use only arrangement, the nasal spray pump 1 can be modified to physically retain the stem 9 in the second stem position. Although not illustrated in the drawings, it will be appreciated that when the stem 9 is moved into the second stem position the stem 9 can engage with the cap 5 to retain or lock the stem in that position and prevent movement of the stem 9 back towards the first stem position. This can be achieved in any desired way such as by use of a projection extending from the cap 5 or the stem 9 for engagement in a corresponding recess disposed in the stem 9 or the cap 5 respectively.

In other preferred embodiments (not illustrated) it will be understood that multiple exits for the conduit 12 may be provided at the lower end of the stem to be disposed under the piston 13 when in the first piston position, as desired.

Figure 6:
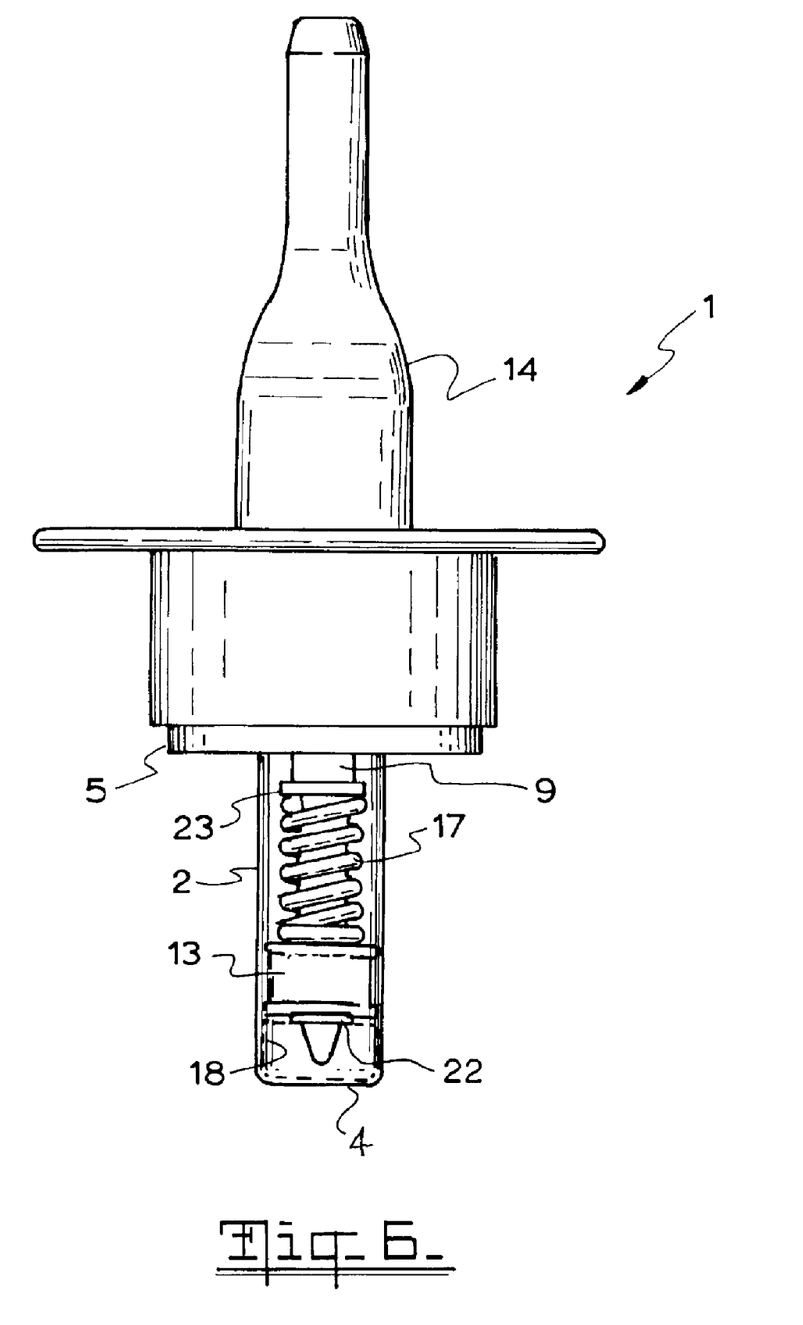
FIG. 6 is a front view of a nasal spray pump according to a second preferred embodiment.
Figure 7:
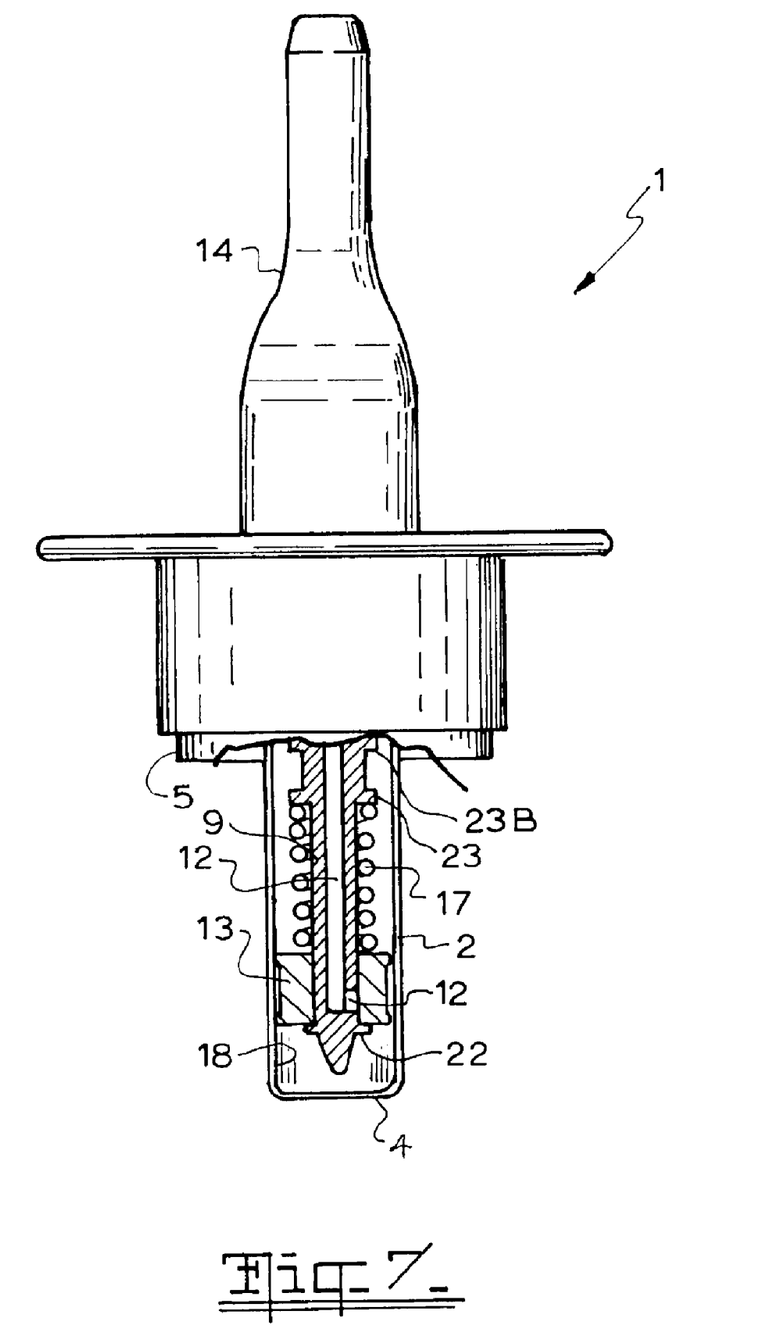
FIG. 7 is a partial cutaway front view of the nasal spray pump of FIG. 7.

Referring now to FIGS. 6 and 7, there is shown a nasal spray pump 1 according to another preferred embodiment. In this second embodiment, it will be appreciated that like reference numerals have been used to denote like components. FIG. 6 is a front view of the nasal spray pump 1 of the second preferred embodiment, and FIG. 7 is a partial cutaway front view of a nasal spray pump 1 of FIG. 6.

In this preferred embodiment, the canister 19 is not used and the reservoir 2 sealingly engages with the collar 5. The piston 13 is resiliently biased into the first piston position, as shown in FIGS. 6 and 7. A slight interference fit between the piston 13 and stem 9 is also provided to provide bias against movement of the piston 13 into the second piston position. A compression spring 17 is disposed about the stem 9 to bias the piston 13 into the first piston position with a predetermined force. The spring 17 is disposed about the stem 9 intermediate the shoulder 23 and the piston 13. The piston 13 is engaged at a lower end at a lower shoulder 22.

As best seen in FIG. 7 a second upper shoulder 23B is spaced apart from the upper shoulder 23 toward the outlet end 10 of the stem 9 is also provided. The second upper shoulder 23B is retained within the collar 5.

It can be seen that in the second embodiment, movement of the stem 9 toward the closed end 3 of the reservoir 2 into the second stem position causes the piston 13 to engage with the piston engagement means 18 to retain movement of the piston 13 whilst allowing downward movement of the stem 9. The spring 17 provides a bias against movement of the piston 13 from the first piston position to the second piston position. As with the first preferred embodiment described in FIGS. 1 to 5, movement of the stem 9 to the second stem position and movement of the piston 13 into the second piston position unseals the exit of the conduit 12 about which the piston 13 is disposed in the first piston position to allow material in the reservoir 2 to be dispensed through the conduit 12 and through the outlet end 10 of the stem 9 for dispensing intra-nasally.

Nasal spray pump head 14 is shown in FIGS. 6 and 7 to facilitate use of the nasal spray pump 1 and delivery of the contents to the users nasal cavity.

The foregoing describes only one embodiment of the present invention and modifications, obvious to those skilled in the art, can be made thereto without departing from the scope of the present invention.

The term "comprising" (and its grammatical variations) as used herein is used in the inclusive sense of "including" or "having" and not in the exclusive sense of "consisting only of".

The invention claimed is:

1. A single dose nasal spray pump comprising:
   a reservoir configured for holding a single dose of material to be dispensed, the reservoir extending between a permanently closed end and an open end;
   a cap to be configured to be disposed over the open end of the reservoir, the cap including an aperture;
   a stem extending between an outlet end and lower end, the stem having a conduit extending from the outlet end of the stem to a conduit inlet at or adjacent to the lower end of the stem; and
   a piston disposed about the stem and configured for movement between a first position wherein the piston seals or substantially seals the conduit inlet and a second position wherein the piston does not substantially seal the conduit inlet;
   wherein the stem is configured for movement from a first stem position wherein the piston is disposed in the reservoir in the first piston position and a second stem position wherein the stem is moved toward the closed end of the reservoir such that the piston is moved into the second piston position.

2. The nasal spray pump according to claim 1 wherein the reservoir includes a piston engagement means disposed a predetermined distance from the reservoir closed end.

3. The nasal spray pump according to claim 2 wherein the piston engagement means includes a radially inwardly projecting seat portion extending a predetermined distance for engagement with the piston when the stem is moved from the first stem position to the second stem position.

4. The nasal spray pump according to claim 1 wherein the stem is configured to be retained in the cap aperture and the stem includes a pair of shoulders spaced apart therealong and configured to be disposed within the inside of the reservoir and wherein a lower shoulder is configured to limit movement of the piston toward the lower end of the stem.

5. The nasal spray pump according to claim 1 wherein the piston engages with the stem in a interference fit.

6. The nasal spray pump according to claim 1 wherein the piston is resiliently biased into the first piston position.

7. The nasal spray pump according to claim 4 including a spring disposed about the stem intermediate the piston and an upper shoulder.

8. The nasal spray pump according to claim 1 wherein the reservoir lower end is shaped such that the lower end of the stem substantially conforms thereto when the stem is moved into the second stem position.

9. The nasal spray pump according to claim 1 wherein the stem is configured to be retained in the stem second position when moved from the first stem position.

10. The nasal spray pump according to claim 1 wherein the cap or the cap aperture engage with the stem when the stem is moved to the second stem position to retain the stem in that position.

11. The nasal spray pump according to claim 1 wherein the outlet end of the stem is configured to receive a nasal spray pump dispensing head.

12. The nasal spray pump according to claim 1 wherein the cap is fixedly mounted to the reservoir or is removably mounted to the reservoir.

13. The nasal spray pump according to claim 1 wherein the cap is configured to be clipped on to, crimped about, or screwed on to the open end of the reservoir.

14. The nasal spray pump according to claim 1 wherein the reservoir is releasably mountable to the cap for replacement of the reservoir subsequent to dispensing material stored in the reservoir.

15. The nasal spray pump according to claim 2 wherein the dose of material to be dispensed is contained in the reservoir at a level at or below the piston engagement means.

16. The nasal spray pump according to claim 1 wherein the lower end of the stem is substantially conical.

17. The nasal spray pump according to claim 1 wherein the open end of the reservoir is sealed or substantially sealed by the cap.

18. The nasal spray pump according to claim 1 including a canister extending between a closed end and an open end, the canister configured to receive the reservoir and to form a seal with the cap.

19. The nasal spray pump according to claim 11 wherein the upper end of the stem is tapered to provide a substantially sealed interference fit with the nasal spray pump head.

20. A nasal spray pump configured to receive a reservoir extending between an open end and a permanently closed end and configured to contain a predetermined dose of material to be delivered intranasally, the nasal spray pump comprising:
　a sealing cap adapted to releasably engage with the reservoir;
　a stem slidable relative to the sealing cap and extending between an outlet end and a lower end, the stem having a conduit extending from the outlet end of the stem to a conduit inlet at or adjacent to the lower end of the stem; and
　a piston disposed about the stem and configured for movement between a first position wherein the piston seals or substantially seals the conduit inlet and a second position wherein the piston does not substantially seal the conduit inlet;
　wherein the stem is configured for movement from a first stem position wherein the piston is disposed in the reservoir in the first piston position and a second stem position wherein the stem is moved toward the closed end of the reservoir such that the piston is moved into the second piston position.

* * * * *